(12) United States Patent
Hong et al.

(10) Patent No.: US 10,166,560 B2
(45) Date of Patent: Jan. 1, 2019

(54) CONTINUOUS LAUNCHER

(71) Applicant: AGENCY FOR DEFENSE DEVELOPMENT, Daejeon (KR)

(72) Inventors: Yunky Hong, Cheongju-si (KR); Kwanho Moon, Daejeon (KR); Byungjin Park, Incheon (KR)

(73) Assignee: AGENCY FOR DEFENSE DEVELOPMENT, Daejeon (KR)

( * ) Notice: Subject to any disclaimer, the term of this patent is extended or adjusted under 35 U.S.C. 154(b) by 225 days.

(21) Appl. No.: 15/028,471

(22) PCT Filed: Dec. 2, 2015

(86) PCT No.: PCT/KR2015/013037
§ 371 (c)(1),
(2) Date: Apr. 11, 2016

(87) PCT Pub. No.: WO2017/069330
PCT Pub. Date: Apr. 27, 2017

(65) Prior Publication Data
US 2017/0259284 A1   Sep. 14, 2017

(30) Foreign Application Priority Data

Oct. 23, 2015   (KR) .......................... 10-2015-0148255

(51) Int. Cl.
*F41B 11/80*   (2013.01)
*B05B 9/047*   (2006.01)
(Continued)

(52) U.S. Cl.
CPC .............. *B05B 9/047* (2013.01); *F41B 11/64* (2013.01); *F41B 11/80* (2013.01); *G01N 3/36* (2013.01); *G01N 3/56* (2013.01); *G01N 3/567* (2013.01)

(58) Field of Classification Search
CPC .. F41A 1/04; F41C 27/06; F41B 11/00; F41B 11/72; F41B 11/721; F41B 11/722; F41B 11/73; F41B 11/80; F41B 11/64
(Continued)

(56) References Cited

U.S. PATENT DOCUMENTS 3,465,639 A * 9/1969 Cooley ..................... F41F 1/00
102/325
3,468,217 A * 9/1969 Cooley ..................... F41F 1/00
42/76.01
(Continued)

FOREIGN PATENT DOCUMENTS

JP   H0339896 A   2/1991
JP   04073795 U1   6/1992
(Continued)

*Primary Examiner* — Jonathan C Weber
(74) *Attorney, Agent, or Firm* — Scully Scott Murphy and Presser; Frank DiGiglio

(57) ABSTRACT

The present disclosure provides a continuous launcher including a pressing tube having a first hollow portion therein, a launch unit having a second hollow portion therein, disposed at a front side of the pressing tube in a spaced manner, and launching a launch object using air compression force, a piston supply unit provided at a rear side surface of the pressing tube, including a plurality of pistons therein, and supplying the pistons one by one, a piston loading unit connected to a rear end of the pressing tube, and moving the piston to a load position, and an operating fluid supply unit supplying an operating fluid to press forward the piston, wherein the launch unit includes a launch tube having a launch hollow portion with the launch object therein, and a diaphragm.

2 Claims, 5 Drawing Sheets

(51) Int. Cl.
  *G01N 3/36*    (2006.01)
  *G01N 3/56*    (2006.01)
  *F41B 11/64*   (2013.01)

(58) Field of Classification Search
  USPC .............................. 124/71–77; 89/7; 42/105
  See application file for complete search history.

(56) References Cited

U.S. PATENT DOCUMENTS

| | | | | |
|---|---|---|---|---|
| 3,601,061 A * | 8/1971 | Dardick | .................... | F41A 9/27 |
| | | | | 102/434 |
| 3,724,114 A * | 4/1973 | Jones | ..................... | F41A 19/58 |
| | | | | 42/106 |
| 3,748,953 A * | 7/1973 | Godfrey | .................... | F41A 1/04 |
| | | | | 239/101 |
| 3,763,740 A * | 10/1973 | Fletcher | .................... | F41F 1/00 |
| | | | | 102/532 |
| 3,791,303 A * | 2/1974 | Sweeney | ................. | F42B 12/40 |
| | | | | 102/502 |
| 4,004,566 A * | 1/1977 | Fischer | .................... | F41A 9/25 |
| | | | | 124/51.1 |
| 4,231,283 A * | 11/1980 | Malburg | ................ | B05B 12/06 |
| | | | | 175/67 |
| 4,341,147 A * | 7/1982 | Mayer | ...................... | F41A 1/04 |
| | | | | 89/7 |
| 4,523,507 A * | 6/1985 | Magoon | .................... | F41A 1/04 |
| | | | | 89/1.1 |
| 4,523,508 A * | 6/1985 | Mayer | ...................... | F41A 1/04 |
| | | | | 89/7 |
| 4,603,615 A * | 8/1986 | Ashley | ..................... | F41A 1/04 |
| | | | | 137/512.1 |
| 4,745,841 A * | 5/1988 | Magoon | .................... | F41A 1/04 |
| | | | | 89/7 |
| 7,299,796 B2 * | 11/2007 | Kirwan | ................... | F41B 11/62 |
| | | | | 124/71 |
| 7,686,005 B2 * | 3/2010 | Adams | ..................... | F41A 1/04 |
| | | | | 124/77 |
| 8,256,406 B1 * | 9/2012 | Kirkpatrick | ........... | F41B 11/723 |
| | | | | 102/440 |
| 8,826,792 B1 | 9/2014 | Granger | | |
| 2010/0212481 A1 * | 8/2010 | Koth | ........................ | F41A 1/00 |
| | | | | 89/7 |
| 2011/0232618 A1 * | 9/2011 | Gabrel | ................. | F41B 11/723 |
| | | | | 124/73 |

FOREIGN PATENT DOCUMENTS

| | | | |
|---|---|---|---|
| JP | 05052727 | A | 2/1993 |
| JP | 06323978 | A | 11/1994 |
| JP | H06323951 | A | 11/1994 |
| JP | H0791887 | A | 4/1995 |
| JP | 01152241 | U1 | 10/1999 |
| JP | 2004271216 | A | 9/2004 |
| JP | 2005262959 | A | 9/2005 |
| JP | 201175307 | A | 4/2011 |
| JP | 201437268 | A | 7/2014 |
| KR | 20140049716 | A | 4/2014 |
| KR | 101401834 | B1 | 5/2014 |
| KR | 10201500611 | A | 6/2016 |

* cited by examiner

CONTINUOUS LAUNCHER

TECHNICAL FIELD

The present disclosure relates to a continuous launcher, capable of continuously launching or spraying (injecting) small ice particles having a diameter of several millimeters (mm), other solid objects to be launched, liquid jet or the like.

BACKGROUND ART

In general, a particle erosion test for various materials is carried out by repetitively performing a unit test of colliding a test sample at the same velocity up to several hundreds of times at the maximum until destroyed. The unit test is also performed repetitively at various collision velocities.

The particle erosion test often requires for a repetitive collision unit test over several thousands of times. To enable a repetitive test at various speed ranges, it is very important to ensure a stable and efficient continuous launching performance of a continuous launcher which is used for the unit test.

Hereinafter, the related art will be described in more detail with reference to FIG. 1.

FIG. 1 illustrates the related art launcher 10 which has been used for fast launching a solid object to be launched (or solid launch object), which contains ice particles, in order to describe the related art.

At a test preparing step, high-pressure gas is charged or filled in a high-pressure unit 11, and normal-pressure gas is filled in a pressing tube 12. A primary diaphragm 14 blocks between the high-pressure unit 11 and the pressing tube 12 which communicate with each other. A piston 16 is pressed toward the pressing tube 12 in response to the primary diaphragm 14 being exploded due to pressure of the high-pressure gas filled in the high-pressure unit 11.

The piston 16 presses the normal-pressure gas filled in the pressing tube 12 while being pressed forward within the pressing tube 12. A secondary diaphragm 15 is provided to block between the pressing tube 12 and a launch tube 13 which communicates with a front end of the pressing tube 12. When the gas within the pressing tube 12 is pressed by preset pressure or more due to the movement of the piston 16, the second diaphragm 15 is exploded. The explosion accelerates a solid launch object 17 located in the launch tube 13 to be launched.

According to the related art, the primary diaphragm 14 is provided between the high-pressure unit 11 and the pressing tube 12. Accordingly, after the gas supplied from the high-pressure unit 11 has predetermined pressure or more, the gas is supplied into the pressing tube 12 by exploding the primary diaphragm 14.

However, according to another related art illustrated in FIG. 2, a valve 24 is disposed between the high-pressure unit 21 and the pressing tube 22, and the gas obtains predetermined pressure or more before the valve 24 is open or closed. Then, the same operation as the aforementioned related art can be performed.

FIG. 2 illustrates a launcher 20 capable of launching a liquid launch object 27, in a different manner from the launcher 10 launching the solid launch object 17 illustrated in FIG. 1.

The launcher 20 illustrated in FIG. 2 can launch the liquid launch object 27 in a manner of spraying water jet.

First, the high-pressure unit 21 is filled with high-pressure gas over predetermined pressure. The valve 24 is provided between the high-pressure unit 21 and the pressing tube 22. When the valve 24 is open to communicate the high-pressure unit 21 and the pressing tube 22 with each other, the high-pressure gas is supplied into a hollow portion formed within the pressing tube 22. A lead bullet 26 is provided in the hollow portion of the pressing tube 22. The lead bullet 26 is pressed forward when the high-pressure gas is supplied in response to the valve 24 being open.

A nozzle 23 through which the liquid launch object 27 is sprayed is provided at a front end of the pressing tube 22. The nozzle 23 has a shape, diameter of which is getting reduced toward a front side for spraying the liquid launch object 27.

Also, a diaphragm 25 is provided to block between the pressing tube 22 and the nozzle 23 communicating with the front end of the pressing tube 22. When the lead bullet 26 is moved to push and explode the diaphragm 25, the liquid launch object 27 located in the nozzle 23 is pressed and sprayed accordingly. That is, the lead bullet 26 serves to spray water jet by compressing the liquid launch object 27 into a high-pressure state.

According to the related art launchers 10 and 20 illustrated in FIGS. 1 and 2, for re-launching after the launch, the high-pressure unit 11, 21, the pressing tube 12, 22, the launch tube 13 and the nozzle 23 should be disassembled (separated). Also, a re-loading process should be carried out to reinstall the piston 16, the primary diaphragm 14, the secondary diaphragm 15 and the diaphragm 25.

The re-loading process requires for the close attention of an operator who performs a re-loading task, and a predetermined task time.

Specifically, for an ice erosion test, the re-loading task is repeated in a low-temperature test room which is less than 10 degrees below zero, which causes a problem of increasing time and costs spent for an entire test. In addition, inaccuracy of the re-loading task which should be done in such a severe environment, safety-related accidents due to an accumulation of fatigue of the operator, and the like are continuously concerned.

The present invention has invented a continuous launcher which is designed into a detachable type to be replaceable.

DISCLOSURE OF THE INVENTION

An aspect of the detailed description is to provide a continuous launcher, capable of continuously launching a solid or liquid launch object.

Another aspect of the detailed description is to reduce a total test cost by improving a structure of a high-priced pressing tube, which has mainly been damaged due to using high pressure in the related art two-stage gas gun.

To achieve these and other advantages and in accordance with the purpose of the present invention, as embodied and broadly described herein, there is provided a continuous launcher including a pressing tube having a first hollow portion in which a piston is movable, a launch unit having a second hollow portion in which the piston is movable, disposed at a front side of the pressing tube in a manner that a front end of the first hollow portion and a rear end of the second hollow portion face each other, and launching a launch object using air compression force, generated by the piston moving from the first hollow portion to the second hollow portion, a piston supply unit provided at a rear side surface of the pressing tube, including a plurality of pistons therein, and supplying the pistons one by one to a rear end of the first hollow portion, a piston loading unit connected to a rear end of the pressing tube, and moving the piston from a supply position of the piston supplied into the first hollow portion to a load position within the first hollow portion, at which the piston is loaded, and an operating fluid supply unit supplying an operating fluid between the supply position and the load position of the piston to press forward the piston from the load position, wherein the launch unit includes a high-pressure connector having the second hollow portion, a launch tube provided therein with the launch object, having a launch hollow portion serving as a path for launching the launch object, and coupled to a front end of the high-pressure connector for communicating the launch hollow portion with the second hollow portion, and a diaphragm disposed to block between the second hollow portion and the launch hollow portion for generating the air compression force, and exploded when the air compression force reaches preset pressure, so as to launch the launch object.

In accordance with another exemplary embodiment disclosed herein, the continuous launcher may further include a launch portion supply unit storing a plurality of launch portions therein, and replaceably placing the plurality of launch portions sequentially at the front side of the pressing tube using a robot arm.

In accordance with another exemplary embodiment disclosed herein, the launch unit may include a high-pressure connector having the second hollow portion, a nozzle having a forwardly-tapering shape for launching a liquid launch object, and a diaphragm disposed to block between the second hollow portion and the nozzle for generating the air compression force, and exploded when the air compression force reaches preset pressure, so as to launch the launch object.

In accordance with another exemplary embodiment disclosed herein, the launch unit may include a nozzle having a forwardly-tapering shape for launching a liquid launch object, and a diaphragm disposed at a rear end of the nozzle. When the diaphragm is pressed and exploded due to a movement of the piston, the launch object may be sprayed in a pressing manner.

In accordance with another exemplary embodiment disclosed herein, the high-pressure connector may include a primary tapering portion formed at a rear end of the second hollow portion, and having a diameter forwardly decreasing from a cavity with a diameter greater than that of the first hollow portion to a cavity with the same diameter as that of the first hollow portion.

In accordance with another exemplary embodiment disclosed herein, the high-pressure connector may include a secondary tapering portion formed at a front end of the second hollow portion, and having a shape with a diameter increasing backwardly from a cavity with a diameter smaller than that the first hollow portion to a cavity having the same diameter as that of the first hollow portion, so as to stop the piston moving within the second hollow portion and press air within the second hollow portion.

In accordance with another exemplary embodiment disclosed herein, the piston loading unit may include an outer cylinder fixed to the rear end of the pressing tube, an inner cylinder configured to be movable back and forth within the outer cylinder, and a load piston movable back and forth within the inner cylinder, and allowing a new piston to be placed at a supply position when being moved backward, and the piston to be placed at a load position more forward than the supply position when being moved forward. The load piston may include a load bar inserted into the first hollow portion through the inner cylinder and the outer cylinder, and the load bar may be formed in a shape of a bar extending into a shape having the same diameter as that of the first hollow portion. When the inner cylinder and the load piston are moved forward, the piston may be loaded at the load position located more forward than a position of the operating fluid supply unit within the first hollow portion. When only the inner cylinder is moved backward in the forwardly-moved state of the load piston, the load piston may be moved back along with the inner cylinder, in response to the backward-movement of the inner cylinder, which may allow the operating fluid supply unit to supply fluid. When the load piston and the inner cylinder are all moved backward, the piston supply unit may supply one of the plurality of pistons at the supply position.

Advantageous Effect

When a continuous launcher according to the present invention is used, a solid or liquid launch object can continuously be launched. This may result in obtaining more improved accuracy and efficiency of a particle erosion test, than those of the particle erosion test performed according to the related art.

Also, a part of a high-priced pressing tube, which is mainly damaged in the related art two-stage gas gun due to a use of high pressure, can be replaced with a detachable high-pressure connector, which may result in a reduction of a total test cost.

MODES FOR CARRYING OUT THE PREFERRED EMBODIMENTS

Hereinafter, description will be given in more detail of a continuous launcher according to exemplary embodiments disclosed herein, with reference to the accompanying drawings.

A singular representation may include a plural representation unless it represents a definitely different meaning from the context.

Terminology or terms used in this specification and claims should not be construed by being limited to typical meaning or the definition of dictionary, but construed as meaning and conception which coincide with the technical scope of the present invention.

For the sake of brief description with reference to the drawings, the same or equivalent components may be provided with the same or similar reference numbers, and description thereof will not be repeated.

Figure 1:
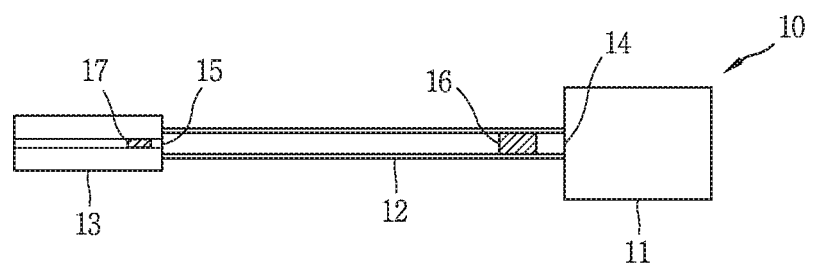
FIG. 1 is a view of a launcher used for fast launching a solid launch object containing ice according to the related art.
Figure 2:
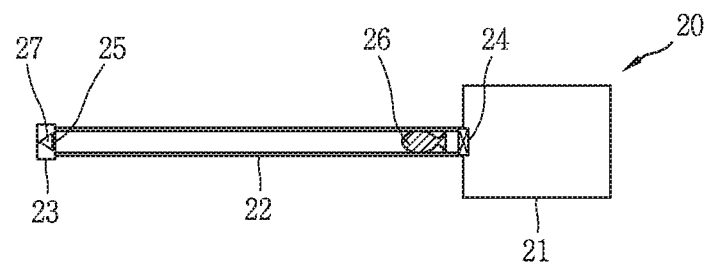
FIG. 2 is a view of another launcher used for fast launching a liquid launch object according to related art.
Figure 3:
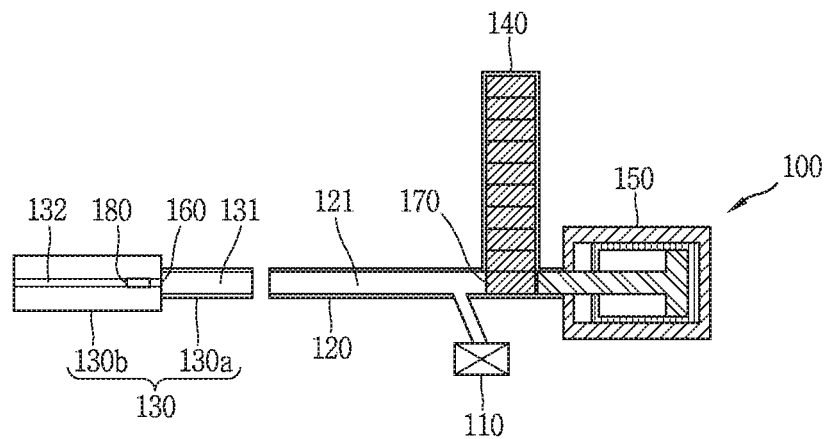
FIG. 3 is a view of a continuous launcher launching a solid launch object in accordance with one exemplary embodiment of the present invention.

FIG. 3 is a view of a continuous launcher 100 launching a solid launch object in accordance with one exemplary embodiment of the present invention.

The continuous launcher 100 may include an operating fluid supply unit 110, a pressing tube 120, a launch unit 130, a piston supply unit 140, and a piston loading unit 150.

The pressing tube 120 may serve to provide a path along which a piston 170 is pressed by pressure of an operating fluid supplied from the operating fluid supply unit 110. The pressing tube 120, to this end, may include a first hollow portion 121 in which the piston 170 is movable.

The launch unit 130 may include, sequentially starting from a front side, a launch tube 130b, a diaphragm 160 and a high-pressure connector 130a.

The high-pressure connector 130a may include a second hollow portion 131 in which the piston 170 is movable. The second hollow portion 131 may have the same cross section as that of the first hollow portion 121.

The launch tube 130b may include a launch hollow portion 132 in which a launch object 180 is movable. The launch hollow portion 132 may have a cross section smaller than that of the second hollow portion 131. With the structure, while the piston 170 moves forward within the second hollow portion 131, it may be stopped without passing through the launch hollow portion 132.

The diaphragm 160 may be configured to block the second hollow portion 131 and the launch hollow portion 132 from communicating with each other. When the diaphragm 160 is exploded, the second hollow portion 131 and the launch hollow portion 132 may communicate with each other. The diaphragm 160 may be exploded when air compression force which is generated by the piston 170 moving from the first hollow portion 121 to the second hollow portion 131 reaches preset pressure, thereby launching a solid launch object 180 which is located at the front of the diaphragm 160.

The launch unit 130 may be disposed at a front side of the pressing tube 120 in a spaced manner. A front end of the first hollow portion 121 and a rear end of the second hollow portion 131 may be disposed to face each other. That is, the launch unit 130 and the pressing tube 120 may be spaced apart from each other.

The operating fluid supply unit 110 may be provided at a rear side surface of the pressing tube 120. When the operating fluid supply unit 110 supplies an operating fluid to the rear side of the piston 170, the piston 170 may be pressed by the operating fluid and thus moved forward along the first hollow portion 121.

The piston supply unit 140 may be provided at a rear side surface of the pressing tube 120. The piston supply unit 140 may include a plurality of pistons 170 therein, and supply the pistons 170 one by one to a rear end of the first hollow portion 121.

That is, for continuous launching after the launch, the piston supply unit 140 may re-supply a new piston 170 to the rear end of the first hollow portion 121. The new piston 170 may be supplied to a supply position located at the rear end of the first hollow portion 121.

The piston loading unit 150 may be provided at the rear end of the pressing tube 120. The piston loading unit 150 may allow the piston 170 to be moved to a load position which is located more forward than the supply position. The load position may be located more forward than the supply position. When the piston 170 is moved from the supply position to the load position, a space for the operating fluid supply unit 110 to supply the operating fluid may be ensured.

That is, the piston loading unit 150 may make the piston 170 moved forward to the load position, such that the operating fluid supply unit 110 can supply the operating fluid. This may enable a movement of the piston 170 in a pressing manner.

Hereinafter, a process of performing continuous launching using the continuous launcher 100 will be described in more detail.

The piston supply unit 140 may supply the pistons 170 one by one to the supply position which is located at the rear end of the first hollow portion 121 of the pressing tube 120.

The piston loading unit 150 may allow the piston 170 to be moved to the load position which is located more forward than the supply position. This may allow for ensuring a space in which the operating fluid supply unit 110 can supply the operating fluid at the rear end of the piston 170.

The operating fluid supply unit 110 may supply the operating fluid into the first hollow portion 121 such that the piston 170 can be pressed forward by the operating fluid. The piston 170 may thusly be fully pressed forward along the first hollow portion 121, and then directly introduced into the second hollow portion 131 formed in the high-pressure connector 130a.

The piston 170 may press air within the second hollow portion 131 while moving along the second hollow portion. The diaphragm 160 may be exploded in response to compression force of the air exceeding preset pressure, and accordingly the solid launch object 180 located at the front of the diaphragm 160 may be pressed and thus launched.

Hereinafter, description will be given in detail of a continuous launcher 200 in accordance with another exemplary embodiment of the present invention.

Figure 4:
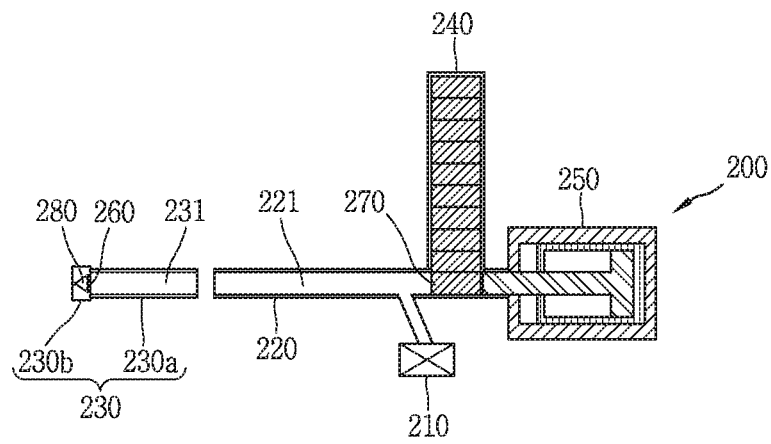
FIG. 4 is a view illustrating a continuous launcher launching a liquid launch object in accordance with another exemplary embodiment of the present invention.

FIG. 4 is a view illustrating a continuous launcher launching a liquid launch object in accordance with another exemplary embodiment of the present invention.

The continuous launcher 200 may include an operating fluid supply unit 210, a pressing tube 220, a launch unit 230, a piston supply unit 240, and a piston loading unit 250.

The pressing tube 220 may include therein a first hollow portion 221 in which a piston 240 is movable.

The launch unit 230 may include, sequentially starting from a front side, a nozzle 230b, a diaphragm 260, and a high-pressure connector 230a.

The high-pressure connector 230a may be provided therein with a second hollow portion 231 in which the piston 270 is movable. The second hollow portion 231 may have the same cross section as that of the first hollow portion 221.

The nozzle 230b may be provided therein with a liquid launch object 280, and have a shape with a forwardly-decreasing diameter. With the structure, while the piston 270 is moved forward within the second hollow portion 231, it may be stopped without passing through the nozzle 230b.

The diaphragm 260 may be provided to prevent the second hollow portion 231 and the nozzle 230b from communicating with each other. When the diaphragm 260 is exploded, the second hollow portion 231 and the nozzle 230b may communicate with each other. The diaphragm 260 may be exploded when air compression force which is generated by the piston 270 moving from the first hollow portion 221 to the second hollow portion 231 reaches preset pressure, thereby launching the liquid launch object 280 which is located at the front of the diaphragm 260.

According to another exemplary embodiment disclosed herein, the launch unit 230 may not include the high-pressure connector 230a, but merely include the nozzle 230b having a forwardly-tapering shape such that the liquid launch object 280 can be launched, and the diaphragm 160 disposed at the rear end of the nozzle 230b.

According to the exemplary embodiment, when the piston 270 is pressed to push and explode the diaphragm 260, the piston 270 may press the launch object 280 to be sprayed.

The launch unit 230 may be disposed at a front side of the pressing tube 220 in a spaced manner. A front end of the first hollow portion 221 and a rear end of the second hollow portion 231 may be disposed to face each other. However, according to the embodiment in which the launch unit 230 does not include the high-pressure connector 230a, the front end of the first hollow portion 221 and the diaphragm 260 may be disposed to face each other. That is, the launch unit 230 and the pressing tube 220 may be spaced apart from each other.

The operating fluid supply unit 210 may be provided at a rear side surface of the pressing tube 220. When the operating fluid supply unit 210 supplies an operating fluid to the rear side of the piston 270, the piston 270 may be pressed by the operating fluid and thus moved forward along the first hollow portion 221.

The piston supply unit 240 may be provided at a rear side surface of the pressing tube 220. The piston supply unit 240 may include a plurality of pistons 270 therein, and supply the pistons 270 one by one to the rear end of the first hollow portion 221.

That is, for continuous launching after the launch, the piston supply unit 240 may re-supply a new piston 270 to the rear end of the first hollow portion 121. The new piston 270 may be supplied to a supply position located at the rear end of the first hollow portion 221.

The piston loading unit 250 may be provided at the rear end of the pressing tube 220. The piston loading unit 250 may allow the piston 270 to be moved to a load position which is located more forward than the supply position. The load position may be located more forward than the supply position. When the piston 270 is moved from the supply position to the load position, a space for the operating fluid supply unit 210 to supply the operating fluid may be ensured.

That is, the piston loading unit 250 may make the piston 270 moved forward to the load position, which may allow the operating fluid supply unit 210 to supply the operating fluid. This may enable a movement of the piston 270 in a pressing manner.

Hereinafter, description will be given of a process of performing continuous launching of the liquid launch object 280 using the continuous launcher 200.

The piston supply unit 240 may supply the pistons 270 one by one to the supply position which is located at the rear end of the first hollow portion 221 of the pressing tube 220.

The piston loading unit 250 may allow the piston 270 to be moved to the load position which is located more forward than the supply position. This may allow for ensuring a space in which the operating fluid supply unit 210 can supply the operating fluid at the rear end of the piston 270.

The operating fluid supply unit 210 may supply the operating fluid into the first hollow portion 221 such that the piston 270 can be pressed forward by the operating fluid. The piston 270 may thusly be fully pressed forward along the first hollow portion 1221, and then directly introduced into the second hollow portion 231 formed in the high-pressure connector 230a.

The piston 270 may press air within the second hollow portion 231 while moving along the second hollow portion 231. The diaphragm 260 may be exploded in response to compression force of the air exceeding preset pressure, and accordingly the liquid launch object 280 located at the front of the diaphragm 260 may be pressed and thus launched in a manner of spraying water jet.

Of course, the piston 270 can be replaced with a load bullet, as described in the foregoing related art launcher. In this instance, the piston supply unit 240 and the piston loading unit 250 may be replaced with a load bullet supply unit and a load bullet loading unit, respectively.

Hereinafter, description will be given in detail of a continuous launcher 300 in accordance with another exemplary embodiment of the present invention.

Figure 5:
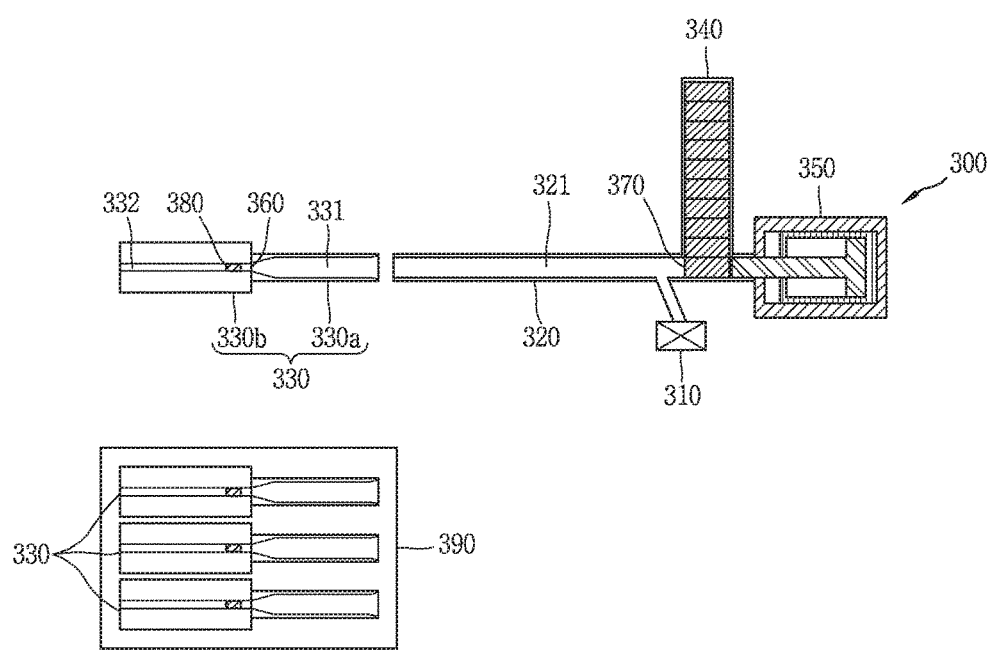
FIG. 5 is a view of a continuous launcher in accordance with another exemplary embodiment of the present invention.

FIG. 5 is a view of a continuous launcher 300 in accordance with another exemplary embodiment of the present invention.

The continuous launcher 300, similar to the aforementioned continuous launchers 100 and 200, may include an operating fluid supply unit 310, a pressing tube 320, a launch portion supply unit 390, a piston supply unit 340, and a piston loading unit 350.

The launch portion supply unit 390 may store a plurality of launch portions 330. The launch portion supply unit 390 may replaceably place the plurality of launch portions 330 one by one at the front side of the pressing tube 320 using a robot arm. Accordingly, after the launch, the used launch portion 330 may be discarded and a new launch portion 330 may be supplied by the launch portion supply unit 390.

Each of the launch portions 330 may include, sequentially starting from a front side, a launch tube 330b, a diaphragm 360, and a high-pressure connector 330a.

In this instance, the high-pressure connector 330a may have a slightly different structure.

Figure 6:
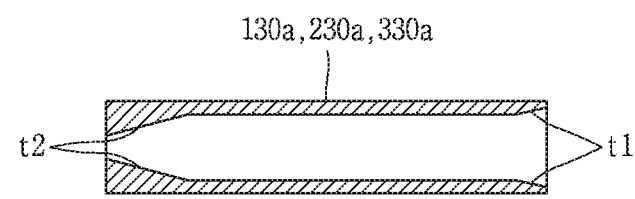
FIG. 6 is an enlarged sectional view of a high-pressure connector in accordance with one exemplary embodiment of the present invention.
Figure 6:
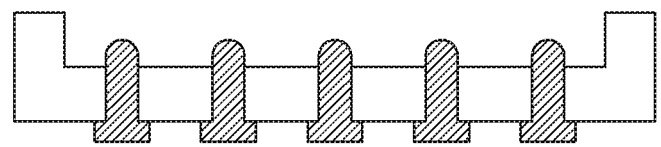
Figure 6:

FIG. 6 is an enlarged sectional view of the high-pressure connector 330a.

The high-pressure connector 330a may be provided therein a second hollow portion 331 in which the piston 370 is movable. The second hollow portion 331 may have the same cross section as that of the first hollow portion 321 at a middle portion except for front and rear end portions of the high-pressure connector 330a.

A primary tapering portion t1 may be formed at a rear end portion of the high-pressure connector 330a. The first tapering portion t1 may have a shape with a cross section decreasing from a cavity with a cross section greater than that of the first hollow portion 321 to a cavity having the same cross section as that of the first hollow portion 321, starting from front to rear ends of the high-pressure connector 330a.

A secondary tapering portion t2 may be formed at a front end portion of the high-pressure connector 330a. The second tapering portion t2 may have a shape with a cross section increasing from a cavity with a cross section smaller than that of the first hollow portion 321 to a cavity having the same cross section as that of the first hollow portion 321, starting from rear to front ends of the high-pressure connector 330a. The secondary tapering portion t2 having such shape may stop the piston 370 which moves forward within the second hollow portion 331. Also, the secondary tapering portion t2 may allow the piston 370 which moves forward within the second hollow portion 331 to more efficiently press air.

Hereinafter, description will be given in more detail of structures and functions of the piston supply unit 140, 240, 340 and the piston loading unit 150, 250, 350.

The piston supply unit 140, 240, 340 and the piston loading unit 150, 250, 350 may have different reference numerals depending on an embodiment to which they are applied. Hereinafter, description will be given of a representative example of applying the components to the continuous launcher 100 illustrated in FIG. 3, and description of other examples of being applied to the other embodiments will be omitted.

Figure 7A:
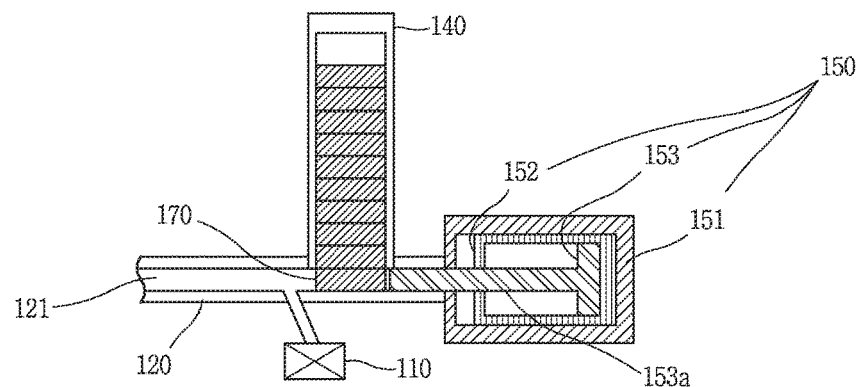
FIG. 7A is a sectional view illustrating operations of a piston supply unit and a piston loading unit in accordance with one exemplary embodiment of the present invention.
Figure 7B:
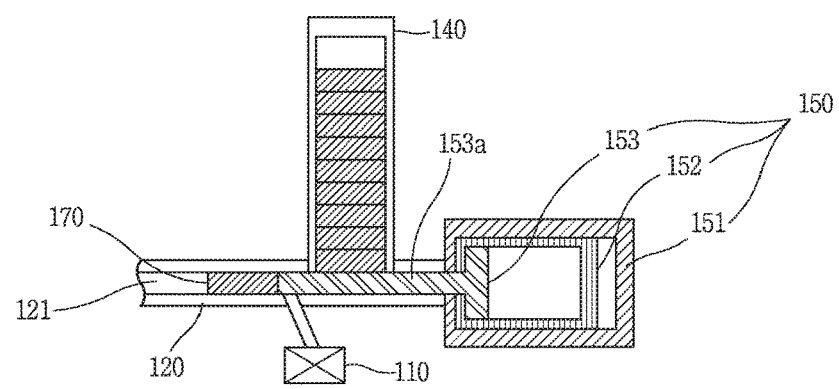
FIG. 7B is a sectional view illustrating operations of a piston supply unit and a piston loading unit in accordance with one exemplary embodiment of the present invention.
Figure 7C:
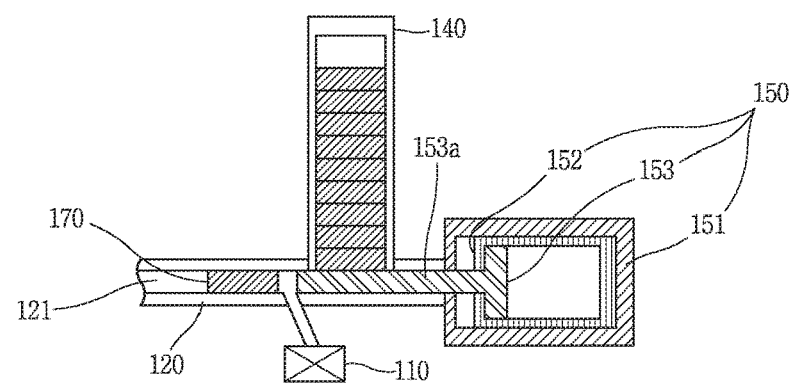
FIG. 7C is a sectional view illustrating operations of a piston supply unit and a piston loading unit in accordance with one exemplary embodiment of the present invention.

FIGS. 7A to 7C are sectional view of the piston supply unit 140 and the piston loading unit 150.

The piston supply unit 140 may be provided at the rear side surface of the pressing tube 120. The piston supply unit 140 may include the plurality of pistons 170 therein. The piston supply unit 140 may supply the pistons 170 one by one to the rear end of the first hollow portion 121.

That is, for continuous launching after the launch, the piston supply unit 140 may re-supply a new piston 170 to the rear end of the first hollow portion 121. The new piston 170 may be supplied to a supply position located at the rear end of the first hollow portion 121.

The piston loading unit 150 may be provided at the rear end of the pressing tube 120. The piston loading unit 150 may allow the piston 170 to be moved to a load position which is located more forward than the supply position. The load position may be located more forward than the supply position. When the piston 170 is moved from the supply position to the load position, a space for the operating fluid supply unit 110 to supply the operating fluid may be ensured.

That is, the piston loading unit 150 may make the piston 170 moved forward to the load position, which may allow the operating fluid supply unit 110 to supply the operating fluid. This may enable a movement of the piston 170 in a pressing manner.

FIGS. 7A to 7C are sectional views illustrating operating steps of the piston loading unit 150.

First, the piston loading unit 150 may include an outer cylinder 151, an inner cylinder 152, and a load piston 153.

The outer cylinder 151 may be fixed to the rear end of the pressing tube 120.

The inner cylinder 152 may be movable back and forth within the outer cylinder 151.

The load piston 153 may be movable back and forth within the inner cylinder 152. The load piston 153 may allow a new piston 170 to be placed at the supply position during a backward movement thereof, and the piston 170 to be placed at the load position more forward than the supply position during a forward movement thereof.

The load piston 153 may include a load bar 153a which is inserted into the first hollow portion 121 through the inner cylinder 152 and the outer cylinder 151, for smoothly performing the aforementioned function.

The load bar 153a may be formed in an extended bar to have a shape corresponding to the cross section of the first hollow portion 121. When the new piston 170 is supplied into the first hollow portion 121, the load bar 153a may be moved forward along the first hollow portion 121 such that the piston 170 can be moved to the load position, and then moved backward again. The operating fluid supply unit 110 may supply the operating fluid into a space which is generated in response to the forwardly-moved load bar 153a moving backward, thereby generating compression force with respect to the piston 170.

Hereinafter, a process of operating the piston loading unit 150 will be described in more detail with reference to FIGS. 7A to 7C.

First, when the inner cylinder 152 and the load piston 153 are moved forward, the piston 170 which has already been supplied may be loaded at the load position located more forward than the position of the operating fluid supply unit 110 within the first hollow portion 121.

In the state that the load piston 153 has been moved forward, when only the inner cylinder 152 is moved backward, the load piston 153 may be moved backward by a backward-movement displacement of the inner cylinder 152, due to the movement of the inner cylinder 152. This may allow for ensuring a space in which the operating fluid supply unit 110 can supply the operating fluid.

When the load piston 153 and the inner cylinder 142 are all moved backward after the launch, the piston supply unit 140 may supply one new piston 170 to the supply position.

Through the repetition of the processes, sequential supply, load and launch of the new piston 170 can be continuously performed.

The invention claimed is:

1. A continuous launcher comprising:
a pressing tube having therein a first hollow portion in which a piston is movable;
a launch unit disposed at a front side of the pressing tube in a spaced manner based on a launching direction, for launching a launch object using compression force, the compression force being generated by the piston moved forward along the first hollow portion;
a piston supply unit provided at a rear side surface of the pressing tube and including therein a plurality of pistons, wherein the piston supply unit supplies the pistons one by one to a rear end of the first hollow portion;
a piston loading unit provided at a rear end of the pressing tube, and allowing the piston to be moved from a supply position of the piston supplied into the first hollow portion to a load position within the first hollow portion, at which the piston is loaded; and
an operating fluid supply unit supplying an operating fluid between the supply position and the load position of the piston, to press forward the piston from the load position,
wherein the launch unit comprises:
a high-pressure connector having therein a second hollow portion, in which the piston is movable; a launch tube having a solid launch object therein, provided with a launch hollow portion serving as a path for launching the solid launch object, the launch tube being connected to a front end of the high-pressure connector to communicate the launch hollow portion and the second hollow portion with each other; and a diaphragm disposed to block between the second hollow portion and the launch hollow portion to generate air compression force within the second hollow portion, and which is exploded to launch the launch object when the air compression force reaches a preset pressure,
wherein the launch hollow portion has a cross section smaller than that of the second hollow portion, wherein the launch unit and the pressing tube are spaced apart from each other, and wherein a front end of the first hollow portion and a rear end of the second hollow portion are disposed to face each other.

2. The continuous launcher of claim 1, wherein the piston loading unit comprises:
an outer cylinder fixed to the rear end of the pressing tube;

an inner cylinder configured to be movable back and forth within the outer cylinder; and
a load piston movable back and forth within the inner cylinder, and allowing a new piston to be placed at a supply position when being moved backward, and the piston to be placed at a load position more forward than the supply position when being moved forward,
wherein the load piston comprises a load bar inserted into the first hollow portion through the inner cylinder and the outer cylinder, and wherein the load bar is formed in a shape of a bar extending into a shape having the same cross section as that of the first hollow portion.

* * * * *